(12) United States Patent
Such et al.

(10) Patent No.: US 7,058,547 B2
(45) Date of Patent: Jun. 6, 2006

(54) DATA ACQUISITION SYSTEM

(75) Inventors: Olaf Such, Aachen (DE); Francisco Morales Serrano, Eindhoven (DE); Stefan Schneider, Aachen (DE); Gereon Vogtmeier, Aachen (JP)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/515,882

(22) PCT Filed: May 19, 2003

(86) PCT No.: PCT/IB03/01916

§ 371 (c)(1),
(2), (4) Date: Nov. 24, 2004

(87) PCT Pub. No.: WO03/099125

PCT Pub. Date: Dec. 4, 2003

(65) Prior Publication Data

US 2005/0216236 A1    Sep. 29, 2005

(30) Foreign Application Priority Data

May 24, 2002  (DE)  ............................... 102 23 309

(51) Int. Cl.
*G06T 15/00*  (2006.01)
(52) U.S. Cl. .............................. 702/189; 378/4; 710/71
(58) Field of Classification Search ..................... None
See application file for complete search history.

(56) References Cited

U.S. PATENT DOCUMENTS

| | | | | |
|---|---|---|---|---|
| 4,135,247 A | * | 1/1979 | Gordon et al. | ................. 378/11 |
| 5,272,627 A | * | 12/1993 | Maschhoff et al. | ............. 378/4 |
| 5,528,043 A | * | 6/1996 | Spivey et al. | .......... 250/370.09 |
| 5,724,037 A | * | 3/1998 | Lee | ............................ 341/143 |
| 5,886,353 A | * | 3/1999 | Spivey et al. | .......... 250/370.09 |
| 6,081,576 A | | 6/2000 | Schanen et al. | |
| 6,272,201 B1 | | 8/2001 | Pan | |
| 6,312,381 B1 | | 11/2001 | Knell et al. | |
| 6,377,902 B1 | | 4/2002 | Eckert | |

FOREIGN PATENT DOCUMENTS

EP    0 597 198 A2    8/1993

* cited by examiner

*Primary Examiner*—Carol S. W. Tsai

(57) ABSTRACT

A data acquisition system which includes data generating and processing units (1a, 1b, 1c), each of which includes a respective data source (3a1, 3a2, 3b1, 3c1) which serves to generate data. The data each time generated is processed by means of associated data processing means (2a, 2b, 2c 11a1, 11a2, 12a1, 12a2, 13a1, 13a2) in such a manner that each time a digital data word which comprises at least two bits is presented for output. The output of the digital data words takes place in synchronous-parallel fashion in dependence on first control signals (4, 5). Shift registers (6a, 6b, 6c) which are coupled to one another so as to form a chain propagate the digital data words in synchronous-parallel fashion in dependence on second control signals (7, 8) and are coupled to a respective associated data generating and processing unit (1a, 1b, 1c).

17 Claims, 6 Drawing Sheets

DATA ACQUISITION SYSTEM

The invention relates to a data acquisition system.

Data acquisition systems are used in types of apparatus which generate data in large numbers or in rapid succession and in which it is necessary that the data is transferred in a defined, disturbance-free manner from the location or locations in which it is generated to the location in which further processing takes place. An apparatus of this kind is, for example, an imaging apparatus such as a medical imaging apparatus in which X-rays incident on a detector are converted into electronic signals, for example, by means of scintillator photodiode units, which electronic signals are, for example, digitized by means of an analog-to-digital converter (ADC). A detector of this kind is typically subdivided into smaller image units or so-called pixels. The data acquisition system is then used to transfer the data generated by the detector pixels and digitized by means of one or more ADCs to another element of the apparatus. A receiving apparatus element of this kind is, for example, an electronic unit which processes the data, a data interface which propagates the data, or a data memory. In the medical field a detector of this kind may inter alia be a high-resolution digital detector for radiographic imaging or an X-ray sensitive detector as used in computed tomography.

A data acquisition system used in such an apparatus is known, for example, from single-line computed tomography apparatus. In a CT apparatus of this kind the detector, being mechanically rigidly attached to the X-ray source, rotates around the object to be examined and it is necessary to acquire and read out projection images from an as adequate as possible number of angular positions. A single-line detector comprises as many as 1000 pixels and is read out approximately 1000 times per second. A typical digitization depth of the pixel data of 16 bits then results in a data rate of $1.6.10^7$ data bits per second. Analog-to-digital converter boards, associated with individual detector modules or with defined groups of pixels and mounted typically at some distance from the detector itself, receive non-amplified analog data from the pixels via analog data leads and amplify and digitize such data which is then applied to the digital data bus via which the digitized data is transferred. For the data rates mentioned the state of the art utilizes conventional (random access) bus systems, for example, PCI or SCSI.

Special requirements are imposed on a data acquisition system when the detector comprises a particularly large number of pixels which must be read out within a short period of time. Contemporary and notably future detectors necessitate very high data rates. Flat digital X-ray detectors may comprise, for example, 2000×2000 pixels on a surface area of 40×40 cm$^2$, all of which have to be read out about every 30 ms. In that case a data acquisition apparatus must transfer $1.33.10^8$ pixel data per second so overall approximately $1.6.10^9$ data bits per second in the case of a digitization depth of, for example, 12 bits. Smaller X-ray detectors (for example, a 20×20 cm$^2$ detector for cardiac examinations) comprise only one quarter of the pixels, so that the data rate is also reduced to one quarter, that is, to $0.4.10^9$ data bits per second. In a contemporary computed tomography (CT) apparatus the number of pixels is substantially smaller (for example, a multi-line CT detector may comprise, for example, 1000×24 pixels, the trend being towards even more lines); however, this data then has to be read out, for example, from 1000 to 1500 times per rotation of the detector system, so that for a desired rotation time of from approximately 0.7 to 0.33 s and a typical digitization depth of approximately 16 bits, the rate is from approximately 0.5 to $1.5.10^9$ data bits per second.

For a data acquisition system for a computed tomography apparatus there is an additional problem in that the relevant detector has a length of approximately one meter; this means that the locations of data generation wherefrom the data ultimately have to be applied to a destination location are situated a corresponding distance apart. The length of a CT detector may, therefore, amount to more than twice the length of a flat X-ray detector.

The use of long analog calbes, therefore, becomes more and more problematic. For example, multi-line detectors involve not only the problem imposed by the increasingly higher density of cables via which the analog data is applied from the detector to the amplifier and the ADC, but also problems in respect of disturbances caused, for example, by a comparatively large cable capacitance in comparison with a small pixel capacitance (determined by a small surface area of the pixel), microphony due to cable motions and interference from electromagnetic fields.

Conventional bus system concepts, for example, as used for single-line detectors, also meet their limits, because reflections (harmonic ringing) occur at the contact areas of the data leads, which reflections could be superposed on the data content in particular in the case of long data leads, so that many disturbances are superposed on the data stream and the data transfer may even become completely impossible. The occurrence of reflections due to so-called harmonic ringing can be suppressed by using special leads adapted to characteristic wave impedances. However, such leads are very expensive. Differential drivers would also be feasible, but the cable density is then increased (because of the necessity to use twisted-pair cables) and the termination of the cables must also be adapted.

The document U.S. Pat. No. 6,081,576 A discloses a scalable data acquisition system for a one-line and a multi-line computed tomography apparatus. Therein, analog data is transferred via cables from detector modules to a data acquisition system backplane. The analog data is resorted on this backplane so that only data of one detector line is coupled to each time one converter board. The analog data is digitized on this converter board and converted into a bit stream. Twelve converter boards are provided for a typical detector line. Each converter board applies its data to the bit data stream at defined instants. The bit stream is transferred from one converter board to another by way of a serial shift register chain and is ultimately applied to a transmission unit.

This data acquisition system is scalable, but the number of converter boards and 1-bit shift register chains increases linearly as a function of the number of detector lines. In the case of 20 detector lines there would be 240 converter boards and 20 serial shift register chains. This solution requires a large amount of surface area and the costs increase linearly.

Therefore, it is an object of the invention to provide an improved and economical data acquisition system for spatially distributed data sources and high data rates. It is also an object of the invention to provide an improved method for data acquisition in the case of spatially distributed data sources and high data rates. It is also an object of the invention to provide an improved X-ray apparatus with a data acquisition system for spatially distributed data sources and high data rates.

The object is achieved by means of a data acquisition system which includes data generating and processing units, each of which includes a respective data source for generating data, data processing means which are arranged to present for output a digital data word which comprises at least two bits and are arranged for synchronous-parallel output of the digital data words in dependence on first control signals, and also includes shift registers which are coupled to one another so as to form a chain and are arranged for synchronous-parallel propagation of the digital data words in dependence on second control signals and are coupled to one of the data generating and processing units.

In this context "synchronous-parallel" is to be understood to mean that the bits of a digital data word which comprises a plurality of bits are output or propagated in parallel (that is, simultaneously) and that such output or propagation takes place synchronously in time for all data generating and acquisition units involved.

The "data" supplied by the data sources may be digital data as well as analog data or a mixture of digital and analog data.

A data acquisition system configured in this manner enables the use of short analog leads, because the data acquisition and processing units are coupled to the shift register chain only by way of digital leads. High bit stream clock rates are reduced to lower digital word clock rates by parallel transmission and the synchronization of the arrangement provides reliable data transmission. The reduction of the digital coupling distance to the coupling between the shift registers also enables an economical implementation of the digital data leads and the drivers.

In conformity with claim 2, at least one data generating and processing unit includes a processing means in the form of an analog-to-digital converter which is coupled to the data source of this unit. This unit can be advantageously used when the data source supplies (fully or partly) analog data which must still be digitized. In accordance with the invention the ADC is arranged near the data source, thus making short analog connections possible.

In conformity with claim 3, at least one data generating and processing unit includes a processing means in the form of a register. When this register has a parallel output for the simultaneous propagation of all bits of a digital data word, parallel output of the digital words is then possible. Moreover, the storage properties of a register can be used to good advantage. For example, a digital data word can be moved to the output of the register while a second digital data word is stored in the register during the next step.

Claim 4 discloses a further special arrangement in accordance with the invention in which one of the data generating and processing units comprises two data sources, each of which is coupled to a respective associated processing means (an ADC), and in which the processing means alternately loads the digital data produced by the ADCs into the register. The digital data need not necessarily be the complete digital data word intended for output.

The embodiment in conformity with claim 5 offers the advantage that a control data bus can be dispensed with when the shift register chain is arranged to propagate also control data. This saves costs and surface area.

In the case where physical measuring variables are to be detected, a data source is to be constructed as a sensor unit in conformity with claim 6.

In the case where, for example, light or X-rays are intended to generate data, in conformity with claim 7 a data source should be arranged to detect electromagnetic radiation.

The embodiment of claim 8 is particularly advantageous in cases involving a very large number of detection elements. The processing elements associated with a data source can then process the data from a plurality of detection elements.

The invention also relates to an X-ray apparatus which includes a data acquisition system in accordance with the invention. Such a data acquisition system can be particularly advantageously used in the case of large dimensions (for example, >20 cm) and/or in the case of high clock rates (for example, >100 Mbits).

The invention notably relates also to a method for the acquisition of data from spatially distributed data sources. This method is disclosed in claim 10.

Various embodiments in accordance with the invention will be described in detail hereinafter with reference to the accompanying drawing.

Figure 1:
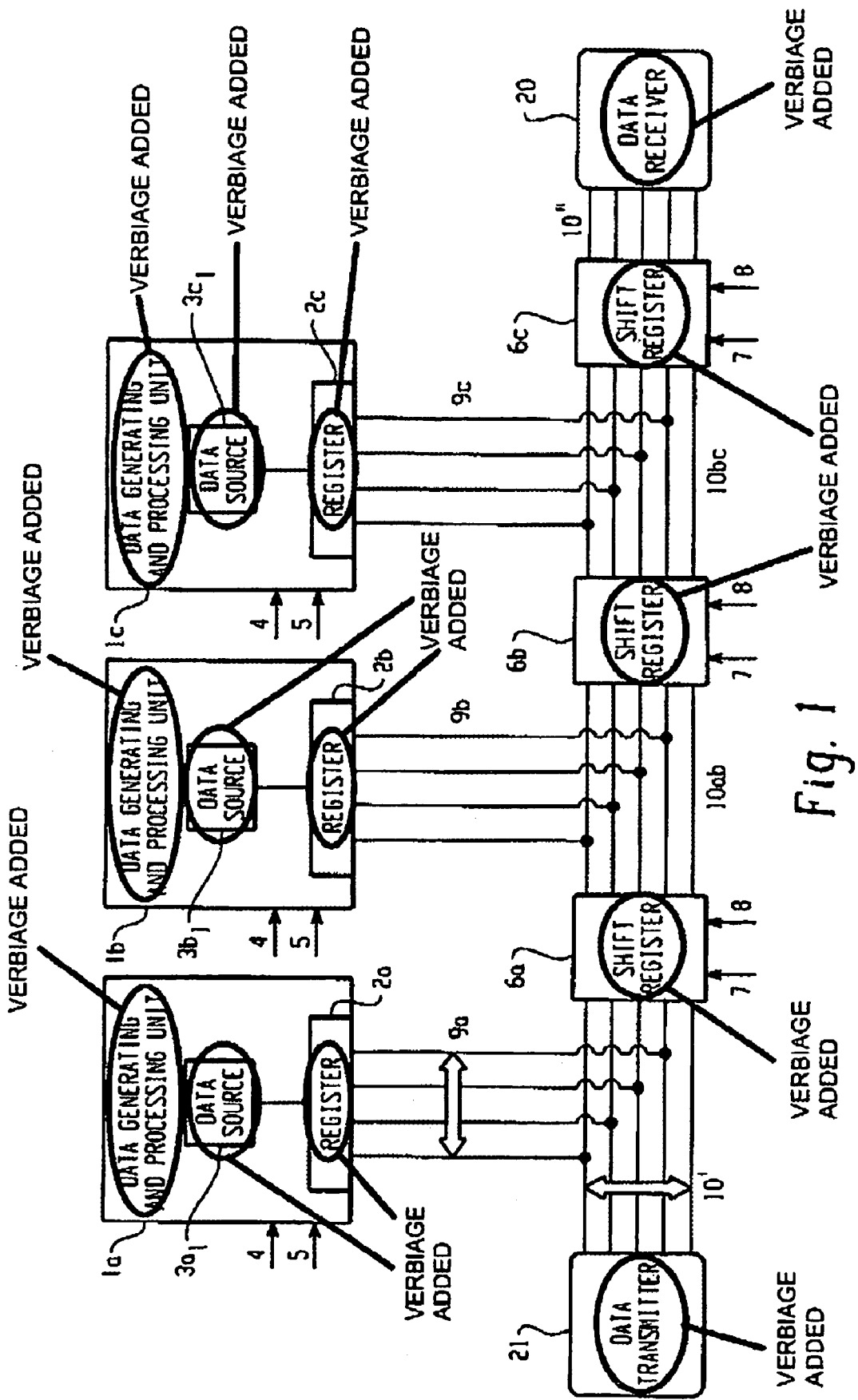
FIG. 1 is a diagrammatic representation of a data acquisition system with data generating and processing units and a chain of shift registers.

FIG. 1 shows an embodiment of a data acquisition system in accordance with the invention. The Figure shows three data generating and processing units $1a$, $1b$, $1c$, which will be referred to hereinafter as units, and three parallel shift registers $6a$, $6b$, $6c$. In this case the shift registers constitute the points for coupling digital data words output by the units into the shift register chain. A data acquisition system may also include only two shift registers or much more shift registers, that is, 10 or 20 or 120. The number of shift registers is determined by the requirements imposed, for example, the expansion of the data acquisition system or the clock rate. In the case of a CT detector, the linear expansion along which the data has to be acquired amounts to approximately 1 m and the data rate amounts to, for example, from $2.10^6$ to $3.10^8$ data words per second in the case of typical multi-line detectors; thus, in the case of 1000 detector columns, 24 detector lines, 1200 projections per revolution and two revolutions per second, it amounts to $57.6.10^6$ data words per second, corresponding to a clock period of approximately 17.4 ns. Each of the units $1a$, $1b$, $1c$ includes a data source $3a_1$, $3b_1$, $3c_1$. Such a data source may, for example, form part of an X-ray detector with a number of pixels adapted to the clock rate that can be realized. There are also provided registers $2a$, $2b$, $2c$ which serve to store digital data words and are configured notably in parallel; for example, the from 2 to 24 bits of a digital data word are then stored simultaneously, without serially loading the individual bits. The units $1a$, $1b$, $1c$ are additionally arranged to receive first control signals 4, 5, for example, clock signals 4 and switching signals 5, in dependence on which the digital data words are propagated further. The units themselves are not connected to one another in this case. In a structurally simple embodiment the data source $3a_1$ forms a unit of a digital data source, for example, a storage means, wherefrom the digital data words are read in dependence on the first control signals 4, 5 so as to be output, for example, via a register $2a$. The data can be read out from the data source $3a_1$ by way of internal or external addressing.

Because of a fully synchronous supply design (for example, as a result of a star-like coupling), the first control signals 4, 5 enable temporally synchronized propagation of the digital data words of a plurality of units via the parallel outputs 2a, 2b, 2c of these units. The control signals 4, 5 enable the defined addressing of individual units, synchronous addressing of a plurality of units or synchronous addressing of all units of the data acquisition system. In the embodiment shown in FIG. 1 a digital data word comprises four bits. The width of the coupling means 9a, 9b, 9c between the units 1a, 1b, 1c and the shift registers 6a, 6b, 6c then corresponds to this bit width of the digital data words. If additional handshake signals or other control signals are also to be transferred, use is made of a coupling means 9a, 9b, 9c which is wider than one digital data word. Coupling means of this kind may be realized, for example, by means of so-called flex foils. The shift registers are coupled so as to form a chain by way of data buses 10ab, 10bc. The shift register chain in this case also comprises a start data bus 10' and an end data bus 10" which serve for coupling data into and out of the shift register chain. For example, the end data bus 10" couples the shift register chain to a data receiver 20, for example, a storage medium or an electronic processing unit. The start data bus 10' couples a data transmitter 21 to the shift register chain. The data transmitter can serve, for example, for coupling control data into the shift register chain. The digital data words propagated by the various units 1a, 1b, 1c need not be limited to the same width as shown in FIG. 1. In a special embodiment one unit propagates a data word having a width of four bits and another unit propagates a data word having a width of eight bits. The coupling means 9a, 9b, 9c should then be configured accordingly. In this case the width of the shift registers 6a, 6b, 6c is at least equal to the width of the widest digital data word to be propagated. Because the synchronous-parallel propagation takes place in a defined manner in dependence on second control signals 7, 8, the data receiver 20 can distinguish the data words of different width. In the case of a CT detector the projection data at the edge of the detector typically have a dynamic range which is smaller than that of those at the center of the detector, and a configuration with different widths reduces the costs and saves space. The data buses 10ab, 10bc in the embodiment shown are configured so as to be wider than the widest digital data word to be transferred (in this case as a data bus with five bits) in order to transfer handshake signals or other control signals. The shift registers 6a, 6b, 6c are arranged to receive two control signals 7, 8, for example, clock signals 7 and switching signals 8, in dependence on which the digital data words are propagated through the chain in a synchronous-parallel manner. As an alternative for the configuration shown in FIG. 1, comprising an unambiguous coupling between a unit and a shift register, it is possible, for example, to couple two units to one shift register. When two units are coupled to the same input of a shift register, for example, the units can be accessed in a temporally alternating fashion. This is advantageous when a clock rate can be realized in the shift register chain which is greater than the data generation period. A further shift register chain can then be dispensed with. In a further alternative embodiment the units are coupled to respective shift registers having a width of at least two digital data words. As a result, two digital data words can be propagated simultaneously per shift register. However, partly overlapping coupling designs are also feasible and/or there may also be more than two units per shift register.

In the case of a multi-line detector of a computed tomography apparatus, for example, digital data having a width of 14 bits or 16 bits can be generated. The digital data word to be transferred often also contains additional scaling bits which indicate which gain stage was selected. In order to cover, for example, a dynamic range of 20 bits, small signals are first amplified before being applied to a digitization unit. For example, a gain of 1, 4, 16 and 64 times can be applied in dependence on the signal level. In order to indicate four gain ranges, an additional 2 bits are required. These two bits are to be added to the digitization depth of, for example, from 14 to 16 bits, so that the digital data word to be propagated comprises from 16 to 18 bits in that case. One gain bit suffices in the case of only two gain ranges. Additional parity bits or error correction bits are also feasible. In the case of other X-ray detectors, customarily data word widths are used which are smaller than in the case of computed tomography. These widths are, for example, from 8 to 12 bits in the case of radiography detectors (for example, image intensifiers or digital flat detectors). When the data acquisition system is used, for example, for digital music data, digital word widths of 24 bits are feasible.

A CT detector is typically constructed from detector modules in the longitudinal direction, for example, modules which comprise 16 columns in the case of a 24-line detector. Each detector module then comprises. When the detector comprises 64 modules, the number of columns amounts to 1024. The typical width of a CT detector pixel amounts to 1 mm, so that the length of such a detector amounts to approximately 1 m. When the data of a module is coupled into a shift register, the shift register chain in this case comprises 64 shift registers.

Figure 2:
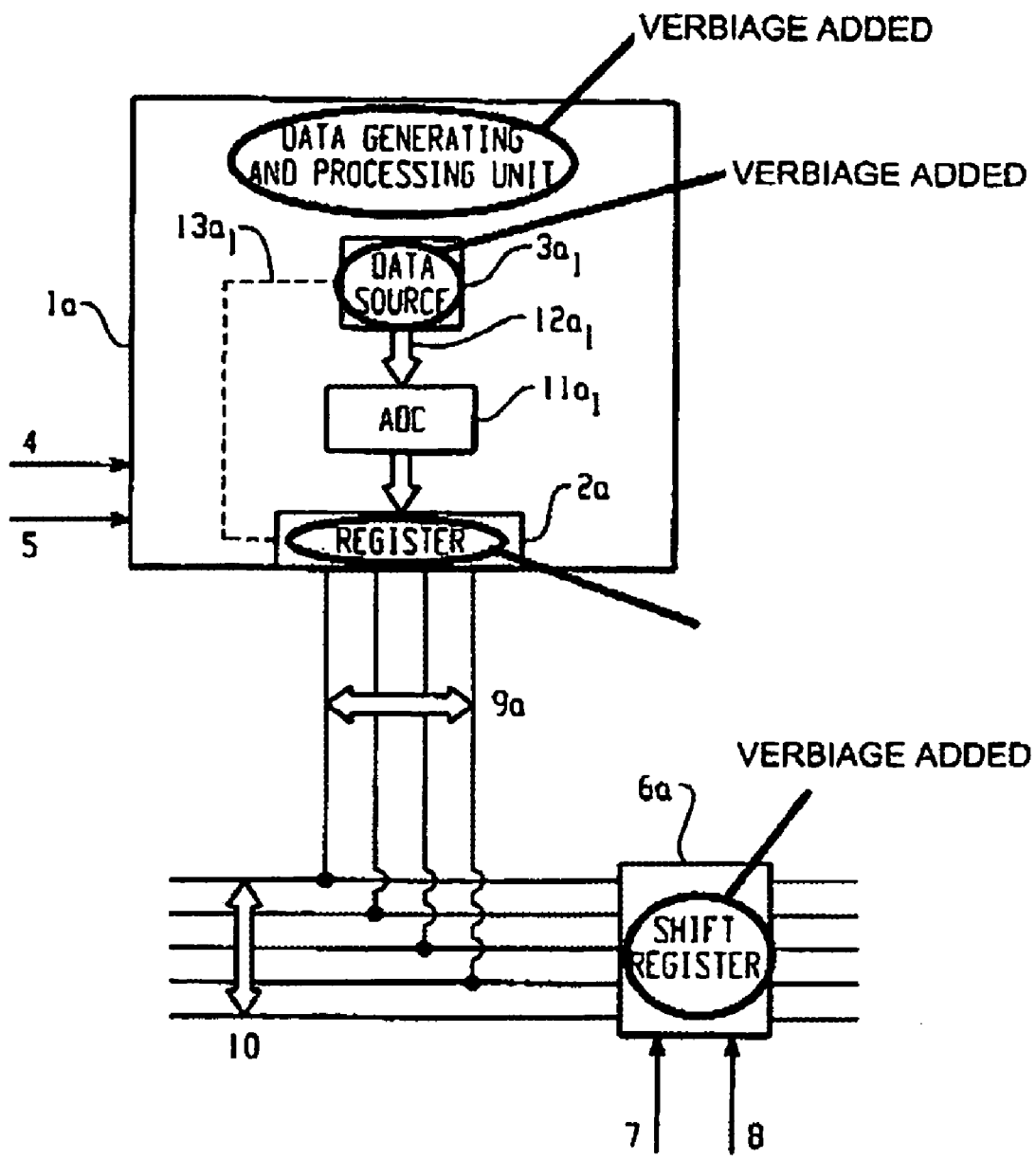
FIG. 2 shows an embodiment of a data generating and processing unit.

FIG. 2 is a detailed illustration of an embodiment of a shift register 6a in the shift register chain with an associated unit 1a. The unit includes a data source 3a$_1$ which is coupled to a digitization unit 11a$_1$ which converts the analog data stream from the data source 3a$_1$ into digital data words. The digitization unit 11a$_1$, for example, an analog-to-digital converter, is coupled to the data source via analog data leads 12a$_1$ and to the register 2a. In an extended embodiment an additional coupling exists between the data source 3a$_1$ and the register 2a via a data lead 13a$_1$ which bypasses the digitization unit 11a$_1$. This is advantageous when the data source 3a$_1$ delivers not only the analog data but also digital data, for example, the described gain factor bits. In the case of a configuration comprising a multi-line computed tomography apparatus, the data source 3a$_1$ is formed, for example, by a photodiode arrangement over which scintillator crystals are arranged so as to convert X-ray quanta into optical light quanta which are converted into a current signal by the photodiodes. In this embodiment an amplifier unit which is associated with the photodiodes also forms part of the data source. The amplifier unit converts, for example, the current signal into a voltage signal. The amplifier unit can be configured for automatic amplification of small signals. The gain factor can then be digitally propagated by way of gain range bits. Using the first control signals 4, 5 and a buffer means (not shown), the coupling of the digital signal to the register 2a can be performed in synchronism with the digitized analog signal. An advantageous embodiment is formed by arranging the digitization unit 11a$_1$ close to the data source 3a$_1$, for example, on the same board outside or shielded from the X-ray beam. The analog leads 12a$_1$ are then very short; they can be realized, for example, as printed wiring of leads having a length of from a few millimeters to a few centimeters.

Figure 3:
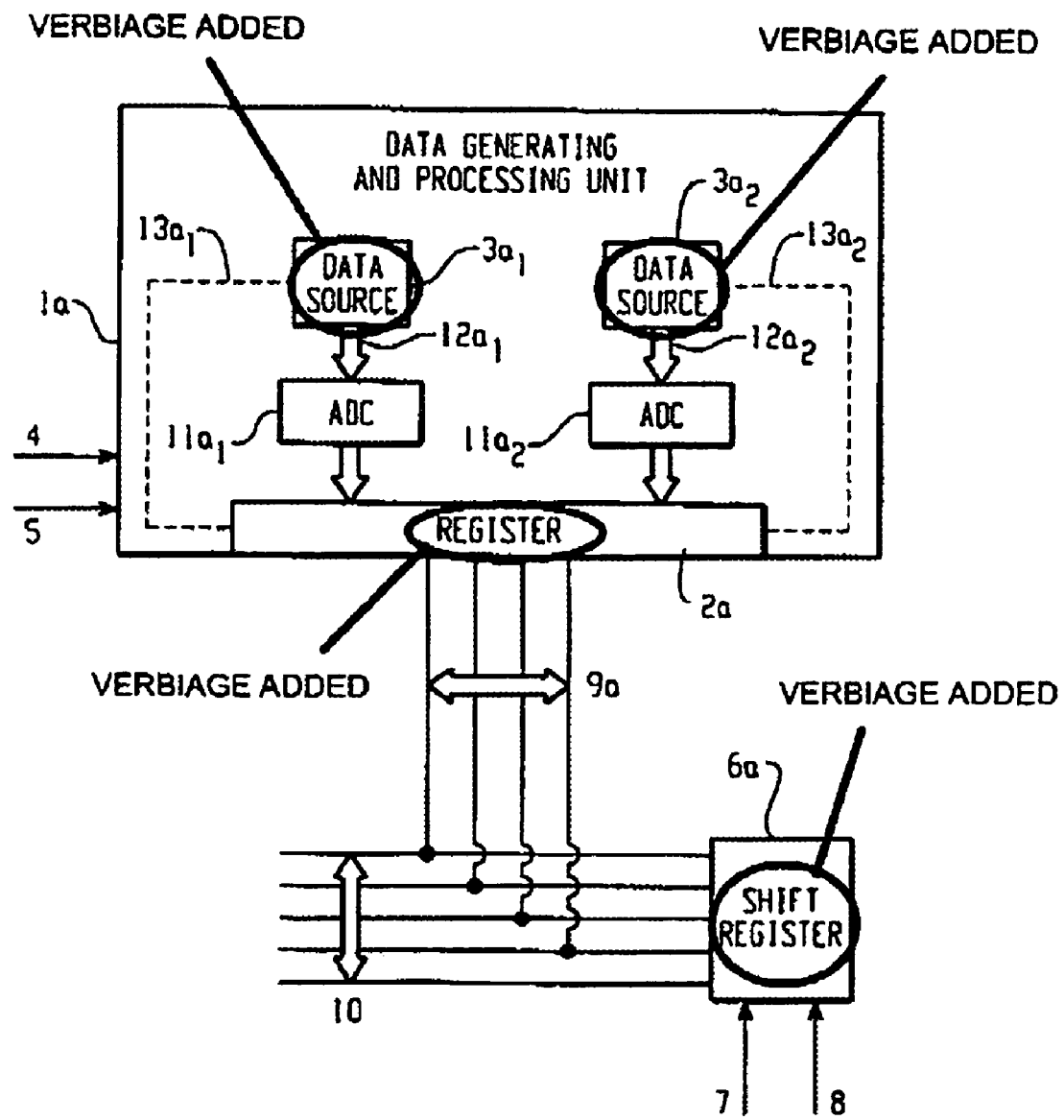
FIG. 3 shows an alternative embodiment of a data generating and processing unit.

FIG. 3 shows a further embodiment of the unit 1a associated with a shift register 6a. The unit 1a in this embodiment includes two data sources 3a$_1$, 3a$_2$ and two digitization units $11a_1$, $11a_2$ which are coupled to these data sources via analog data leads $12a_1$, $12a_2$. The digitization units $11a_1$, $11a_2$ are coupled to the register 2a. This embodiment makes sense when the duration of the digitization of the data, generated by the data sources $3a_1$, $3a_2$, by way of a digitization unit exceeds the desired read-out time. The data sources $3a_1$, $3a_2$ in an embodiment correspond to the upper half and the lower half of a module of a multi-line detector. Thus, in the case of a 24-line detector they correspond to the upper twelve lines and the lower twelve lines, respectively. As described for FIG. 2, expanded embodiments are feasible in which digital data supplied by the data sources $3a_1$, $3a_2$ is applied in synchronism to the register 2a via data leads $13a_1$, $13a_2$. In the case of analog-to-digital converter outputs which can be switched in a high-ohmic fashion, the register can be realized by the output thereof. If the output of the digital data words is realized via a register, this embodiment has the advantage that the storage properties of the register can be utilized, for example, for propagating a digital signal word to the shift register and for storing a second digital data word shortly thereafter, so that the ADCs can already carry out a further conversion. A register can also advantageously receive the data from a digitization unit $11a_1$, $11a_2$ and in synchronism therewith the associated digital data via the data leads $13a_1$, $13a_2$. The addressed registers (also the shift registers) may be edge-controlled as well as level-controlled.

Figure 4:
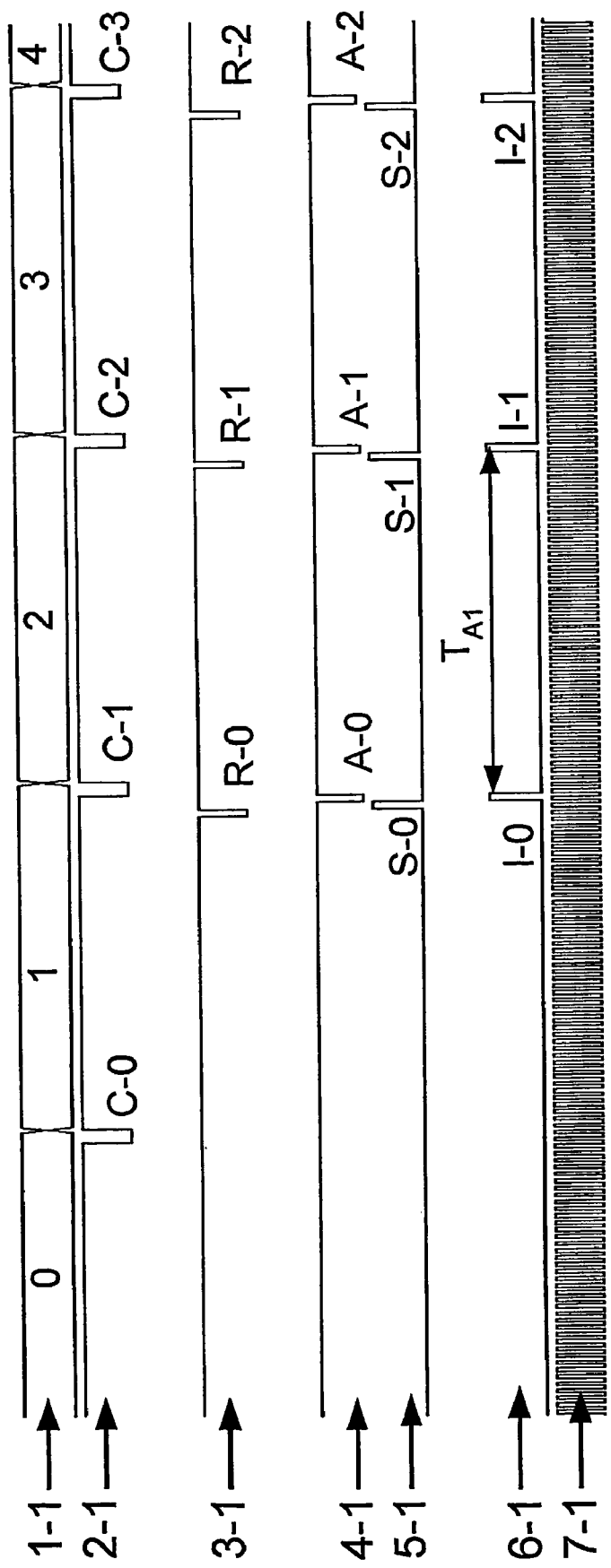
FIG. 4 shows the time diagram for the embodiment of a data acquisition system as shown in FIG. 2.

FIG. 4 shows the beginning of the time diagram of a unit 1a and the associated shift register 6a for the embodiment shown in FIG. 2 which includes a register 2a and an ADC $11a_1$. The data source 3a in this case consists of a plurality of pixels which generate measuring data, for example, by detecting X-rays and converting the X-ray signal into an electric signal. The line 1-1 shows the active detector pixel. The addressing can take place by way of an addressing unit within the unit but also by external addressing, in which case the first control signals 4, 5 additionally comprise the addressing information. The signal on the line 2-1 initiates the start of the conversion of the analog signal from the active detector pixel into a digital signal by means of the ADC $11a_1$ (C-0 starts the conversion of the signal from the pixel bearing the index 0; analogously, C-1 starts the conversion of the signal from the pixel denoted by the reference 1). The ADC result is read from the register 2a by means of the read-out signal 3-1 (R-0 reads out the digitized signal from the pixel 0, etc.). In the next step the clock signal 5-1 applies the value on the input of the register 2a to the output (S-0 initiates the writing of the digitized value of the pixel 0 to the register output, etc.) and subsequently the signal 4-1 activates the output (A-0 activates the output for the value from the pixel 0, etc.). The signals 2-1, 3-1, 4-1 and 6-1 in the embodiment shown obey an inverse logic, that is, the desired event is initiated by a non-active signal. While the output of the unit 1a is active, the output of the associated shift register 6a is inactive because of the inverse logic of the signal 6-1 (1-0 sets the output of the shift register to the inactive state while the value of the pixel 0 is transferred to the shift register, etc.). The activation of the output of the register 2a takes place in temporal synchronism for all units 1a, 1b, 1c of the data acquisition system. The digital data word bits are transferred in parallel, that is, simultaneously, via the coupling means 9a, 9b, 9c. Subsequently, digital data words are present on the inputs of all shift registers 6a, 6b, 6c. During the next step, the output of the shift register 6a is activated and, using the clock signal 7-1, the contents of the shift register chain are propagated in synchronized form until the next activation of the outputs 2a, 2b, 2c of the units 1a, 1b, 1c, so that all data is propagated to the data receiver 20. The shift register chain is then empty and digital data words can again be applied to the inputs of the shift registers. If the read-out procedure is to be repeated after the complete reading out of all detector module pixels, as it may be desired as many as approximately 3000 times per rotation, in dependence on the type of CT scanner, the further read-out procedure can follow contiguously. In this embodiment the signals 1-1, 2-1, 3-1, 4-1 and 5-1 are to be understood as the first control signals 4, 5 and the signals 6-1 and 7-1 as the second control signals 7, 8.

Figure 5:
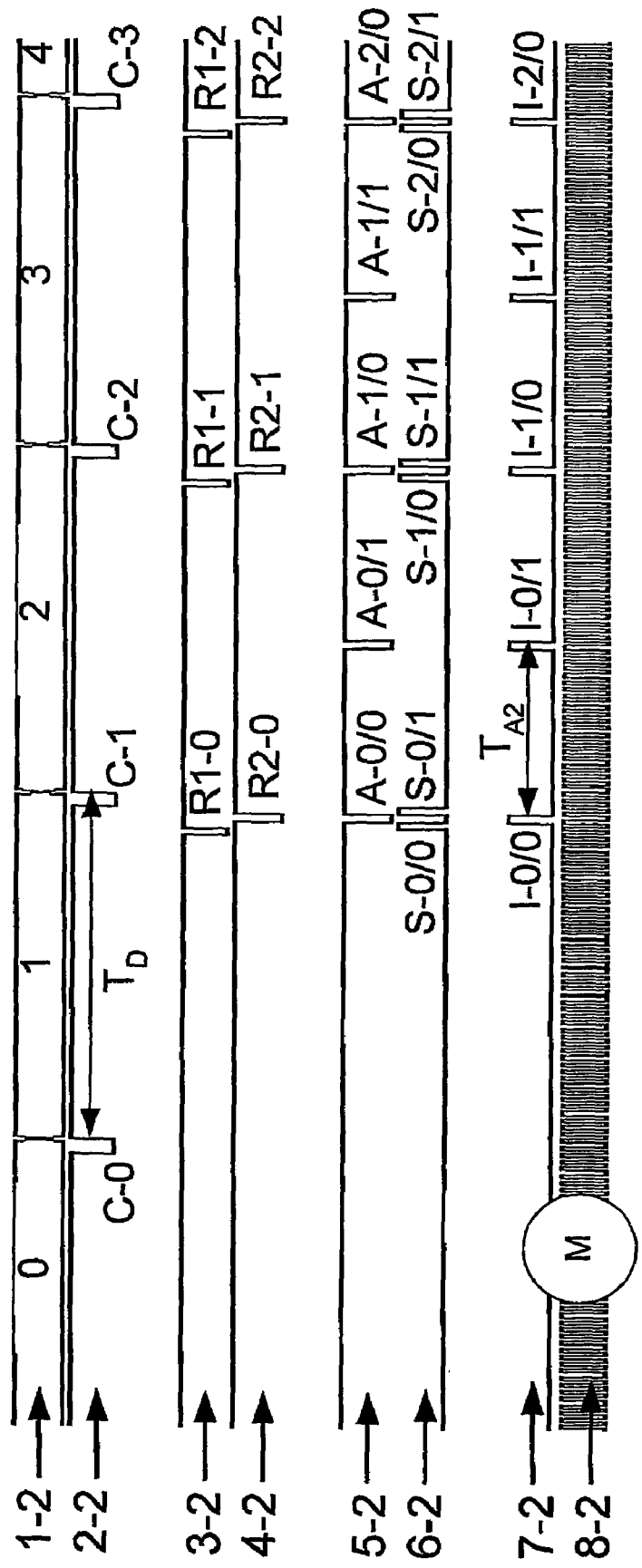
FIG. 5 shows the time diagram for the embodiment of a data acquisition system as shown in FIG. 3.

FIG. 5 shows the beginning of the time diagram in the case of an embodiment as shown in FIG. 3 which comprises two ADCs $11a_1$, $11a_2$ for all units and a respective register 2a, 2b, 2c. The reference 1-2 of the signals denotes the addressing index of the active pixel and the reference 2-2 the start of the conversion (in synchronism for both ADCs); 3-2 and 4-2 denote the read-out signal for the first and the second ADC, 5-2 denotes the activation signal for the output of the register 2a, 6-2 denotes the clock signal for propagating the signal to the output, 7-2 denotes the activation signal for the output of the shift registers 6a, 6b, 6c and 8-2 denotes the clock signal for the shift registers 6a, 6b, 6c. The signals 2-2, 3-2, 4-2, 5-2 and 7-2 operate with inverse logic. In this embodiment the ADCs convert their input signals in synchronism (thus, C-0 starts the conversion of the pixel of the first data source $3a_1$ which is denoted by the reference 0 and in synchronism the conversion of the pixel of the second data source $3a_2$ which is denoted by the reference 0), but the ADC a $11a1$ is read out first (initiated by the read-out signal 1-0 for the conversion result of the pixel 0), the result thereof being applied to the output of the register 2a (by way of the signal S-0/0 for the pixel 0). After this result has been propagated by activation of the output of the register 2a (by the signal A-0/0 for the pixel 0), the result of the second ADC $11a_2$ is applied to the output of the register 2a (by means of the signal S-0/1 for the pixel 0). After the shift register chain has been emptied, the output of the register 2a is activated again (by means of the signal A-0/1 for the pixel 0). In this case the signals 1-2, 2-2, 3-2, 4-2, 5-2 and 6-2 are the first control signals 4, 5 and the signals 7-2 and 8-2 are the second control signals 7, 8. The control, that is, the activation, of the outputs of the registers 2a, 2b, 2c and the deactivation and clocking of the shift registers 6a, 6b, 6c take place in synchronism.

Figure 6:
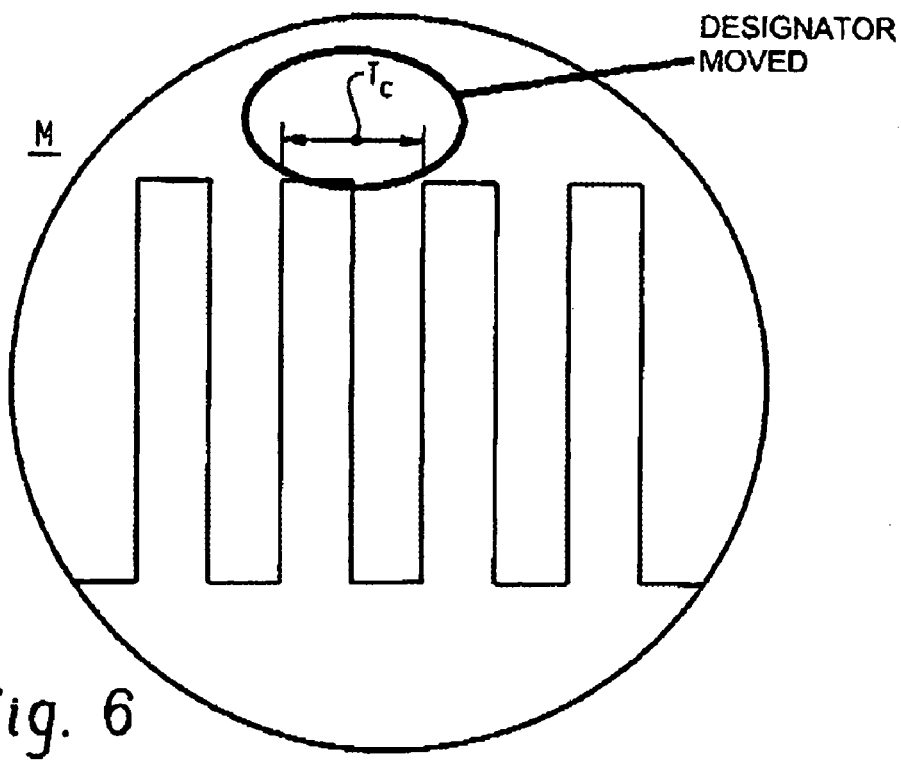
FIG. 6 shows a part of the clock signal variation in the shift registers.

FIG. 6 is an enlarged representation of the part of the clock signal of FIG. 5 which is denoted by the reference M. The distance between two clock pulses is denoted by the reference $T_C$. In the embodiment shown in FIG. 4 the distance $T_{A1}$ between two synchronous propagations of digital data words of the units 1a, 1b, 1c on the shift registers 6a, 6b, 6c should be chosen to be such that the propagations through the shift register chain which take place at the distance $T_C$ have shifted the data out of the chain so that repeated storage will not erase old data. In the embodiment shown in FIG. 5 the distance $T_{A2}$ between two synchronous coupling in operations for the digital data words from the units 1a, 1b, 1c to the parallel shift registers 6a, 6b, 6c should be selected analogously. In the embodiment shown the number of clock signals 8-2 between the individual activations (for example, between A-0/0 and A-0/1) amounts to only half the number in the embodiment shown in FIG. 4. The data acquisition system shown in FIG. 5, therefore, comprises only half the number of shift registers present in the embodiment shown in FIG. 4. For the same clock signal duration, however, the number of data read out is exactly the same, but in this embodiment half the number of coupling means 9a, 9b, 9c can be dispensed with. When the read-out duration is determined by the conversion duration, that is, by the distance $T_D$ required between the starts of the conversion (for example, between C-0 and C-1), in the embodiment shown in FIG. 5 the conversion duration TD may amount to twice the read-out duration $T_{A2}$.

Because the shift registers 6a, 6b, 6c are coupled so as to form a chain, the digital data words are unidirectionally propagated to the data receiver 20. The start data bus 10' of the chain in an advantageous embodiment can be used to input control data, for example, by way of a data transmitter 21. The control data is also propagated through the chain, for example, before or after a data read-out cycle or, for example, during a data read-out cycle, the coupling in of control data and the reading-out of digital data words then being controlled via an appropriate time diagram. Flag bits in the control data or, for example, a flag digital data word supplied in advance, then enable defined control of the destination so that corresponding read means, accessing the shift register chain, recognize, for example, by way of access to the output of the shift register, that the next data item is intended for these means or that a given set of data is intended for these means. This ultimately enables control and/or configuration of associated units. The use of the shift register chain for the supply of control data (which data may comprise local program updates, calibration data, requests for a self-check etc.) makes an additional control data bus superfluous, thus saving costs and space.

Figure 7:
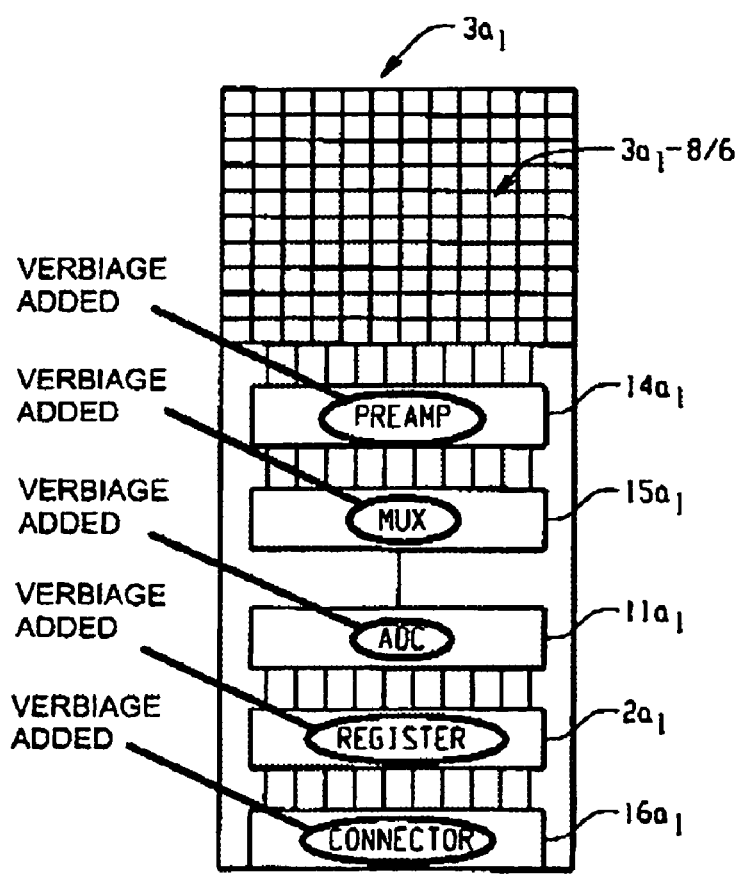
FIG. 7 illustrates an example of a CT detector module.

FIG. 7 illustrates an example of a CT detector module. When modules of this kind are linked by way of their longitudinal sides, the data source 3a₁, being arranged to detect X-rays in the present case, forms a multi-line X-ray detector. In the embodiment shown the X-ray-sensitive sensor is formed by a plurality of X-ray-sensitive pixels (the pixel from the column 8 and the line 6 is denoted by the reference 3a₁-8/6 by way of example). The charge carriers generated by the pixels by conversion of the X-rays are stored in the pixel capacitance or in additional capacitances during an integration period and either are read out directly or transferred to a sample-and-hold buffer at a given instant. Using preamplifiers 14a₁, the charge signals are amplified and converted into voltage signals which are applied to an ADC 11a₁ by means of a multiplexer 15a₁ in the present embodiment, after which the digitized data is applied in parallel to a register 2a₁. In the case of an active register output, the digital data words are then applied, via a connector 16a₁ and a flexible cable connected thereto, to the shift register chain. A CT detector module typically also includes further electronic components, for example, for receiving the control signals which are not shown in this Figure.

In an example of an embodiment the units are restricted in space; for example, they are smaller than 100 cm². In the case of a CT detector module comprising 16 columns, the unit would have a width of approximately 1.6 cm and should not be deeper than approximately 10 cm, resulting in a surface area of 16 cm². The analog data leads between preamplification and ADC are then limited to no more than a few centimeters.

The clock rate for data propagation in the shift register chain can be very high. When the number of shift registers is also high, the distance between these shift registers amounts to only a few centimeters. Such a transmission path can be realized also in the case of high clock rates, that is, without using expensive cables or intricate drivers. The clock rate between the units 1a, 1b, 1c and the shift registers 6a, 6b, 6c is lower, for example, in proportion to the number of shift registers, than the clock rate in the shift register chain. This allows for the use of longer coupling means 9a, 9b, 9c between the units and the shift registers (lengths of from 10 to 20 cm can be realized). As a result, the shift register chain can be arranged at some distance from the units, for example, underneath the detector.

As a result of the use of a shift register chain and the fully synchronous control of the shift registers and the data generating and processing units, very high clock rates can be achieved in the case of spatially distributed data sources.

The invention claimed is:

1. A data acquisition system which includes:
   data generating and processing units, each of which includes:
      a respective data source for generating data;
      data processing means which are arranged to present for output a digital data word which comprises at least two bits; and are arranged far synchronous-parallel output of the digital data words in dependence on first control signals;
   shift registers which are coupled to one another and each of which:
      is arranged for the synchronous parallel propagation of the digital data words in dependence on second control signals; and
      is coupled to one of the data generating and processing units.

2. A data acquisition system as claimed in claim 1, wherein the data processing means of one of the data generating and processing units include an analog-to-digital converter.

3. A data acquisition system as claimed in claim 1, wherein the data processing means of one of the data generating and processing units includes a register which is arranged to store the digital data words which comprise at least two bits.

4. A data acquisition system as claimed in claim 1, wherein the data processing means of one of the data generating and processing units comprise two analog-to-digital converters, coupled to a respective one of the data sources, and a register which is arranged to load digital data from each time one of the analog-to-digital converters in a temporal alternation.

5. A data acquisition system as claimed in claim 1, wherein the chain of shift registers is arranged to propagate control data.

6. A data acquisition system as claimed in claim 1, wherein one of the data sources is a sensor unit.

7. A data acquisition system as claimed in claim 1, wherein one of the data sources is arranged to detect electromagnetic radiation.

8. A data acquisition system as claimed in claim 7, wherein the data source which is arranged to detect electromagnetic radiation comprises a plurality of detection elements.

9. An X-ray apparatus which includes a data acquisition apparatus as claimed in claim 1.

10. A method for the acquisition of data, which method includes:
    generating of data in a plurality of data generating and processing units by means of a respective data source;
    presentation of digital data words which comprise at least two bits by means of data processing means associated with the data generating and processing units;
    synchronous-parallel output of the digital data words in dependence on first control signals;

synchronous-parallel storage of the digital data words in shift registers, coupled to one another so as to form a chain, in dependence on second control signals; and synchronous-parallel propagation of the digital data words through the chain of shift registers in dependence on the second control signals.

11. A method for the acquisition of data as claimed in claim 10, including using an analog-to-digital converter to generate digital data.

12. A method for the acquisition of data as claimed in claim 10, wherein the shift registers comprise at least two bits.

13. A method for the acquisition of data as claimed in claim 10, including:

using two analog-to-digital converters coupled to a respective data source to generate digital data; and loading the digital data generated by the analog-to-digital converters into a register in temporal alternation.

14. A method for the acquisition of data as claimed in claim 10, wherein the chain of shift registers is arranged to propagate control data.

15. A method for the acquisition of data as claimed in claim 10, wherein the data source is a sensor unit.

16. A method for the acquisition of data as claimed in claim 10, wherein the data source is arranged to detect electromagnetic radiation.

17. A method for the acquisition of data as claimed in 16, wherein the data source which is arranged to detect electromagnetic radiation comprises a plurality of detection elements.

* * * * *